United States Patent [19]

Goswami

[11] Patent Number: 5,281,534
[45] Date of Patent: Jan. 25, 1994

[54] PROCESS FOR HYDROLYZING STEREOISOMER ESTERS OF TRANS CHRYSANTHEMIC ACID USING LIVER ENZYMES DERIVED FROM HORSE, RABBIT, PIGEON OR CAT

[75] Inventor: Animesh Goswami, Princeton, N.J.

[73] Assignee: Rhone-Poulenc Inc., Princeton, N.J.

[21] Appl. No.: 885,923

[22] Filed: May 18, 1992

Related U.S. Application Data

[63] Continuation of Ser. No. 484,797, Feb. 26, 1990, abandoned.

[51] Int. Cl.$^5$ .............................................. C12P 41/00
[52] U.S. Cl. ..................................... 435/280; 435/136
[58] Field of Search ................................ 435/280, 136

[56] References Cited

U.S. PATENT DOCUMENTS

| | | | |
|---|---|---|---|
| 4,650,755 | 3/1987 | Wood et al. | 435/43 |
| 4,985,364 | 1/1991 | Hildebrand et al. | 435/280 X |

FOREIGN PATENT DOCUMENTS 8706269 10/1987 World Int. Prop. O. .......... 435/136

OTHER PUBLICATIONS

Abernathy, CA 80: 606d c1974).
Mitsuta et al., CA 110:113240m (Mar. 27, 1989).
Soderlund et al., CA 87:129395h (1978).
Soderlund, Pest. Biochem & Physiology, 7, 391-401 (1977).
Schneider et al., Angew. Chem. Int. Ed. Eng. 23, (1984).
Sigma Catalog, pp. 952-953, 584 (1989).
Abernathy Co., Pesticide Biochem. Physiol 3:300-11 (1973).
Klibanov AM, TIBS 14:141-144 (1989).

*Primary Examiner*—Douglas W. Robinson
*Assistant Examiner*—S. Saucier
*Attorney, Agent, or Firm*—Paul J. Juettner

[57] ABSTRACT

Chrysanthemic acid esters can be geometrically separated into its cis- and trans- isomers as well as resolved into enantiomers by hydrolysis using liver enzymes, particularly from sheep, goat, bovine, dog, chicken, mouse, calf, horse, pigeon, rabbit, cat, whale and rat and particularly horse.

41 Claims, No Drawings

PROCESS FOR HYDROLYZING STEREOISOMER ESTERS OF TRANS CHRYSANTHEMIC ACID USING LIVER ENZYMES DERIVED FROM HORSE, RABBIT, PIGEON OR CAT

This is a continuation of copending application Ser. No. 07/484,797, filed on Feb. 26, 1990, now abandoned.

FIELD OF THE INVENTION

The present invention relates to the separation of geometric isomers and the resolution of stereoisomers of chrysanthemic acid by the stereoselective hydrolysis of its esters using the liver enzymes of various species.

BACKGROUND OF THE INVENTION

The insecticide deltamethrin ("Synthetic insecticides with a new order of activity", M. Elliot et al., *Nature*, 248, 710–711, 1974) is prepared from both of the enantiomerically pure trans isomers of chrysanthemic acid using the resolved enantiomers and separate processing steps for each enantiomer. The pure enantiomers of trans chrysanthemic acid, in turn, are prepared from the racemic mixture of their diastereomeric salts by crystallization ("Evolution of an industrial process: deltamethrin synthesis", J. Tessler, *Chemistry and Industry*, 199–204, 1984).

The stereospecific hydrolysis of esters by enzymes from animal sources, especially from the livers of various species, has mainly concentrated on the use of enzymes from porcine liver ("Enzymes in organic synthesis", J. B. Jones, *Tetrahedron*, 42, 3351–3403, 1986 and the references cited therein).

The enzymes from the livers of other species have been used only in a limited number of cases for sterospecific hydrolysis. For example, enzymatic resolution of bicyclic lactones using horse liver enzyme has recently been reported ("Enzymatic resolution of bicyclic lactones by horse liver enzyme", E. Guibe et al., Tetrahedron Letters, 30, 67–68, 1989).

The hydrolysis of esters of chrysanthemic acid by enzymes from porcine liver was reported in the literature ("Enzymatic syntheses of Chiral building blocks from racemates: Preparation of (1R, 3R) - Chrysanthemic, - Permethrinic and -Caronic acids from racemic, diastereomeric mixtures", M. Schneider et al., *Angew, Chem. Int. Ed., Engl.*, 23, 64–66, 1984).

Because of the commercial importance of trans chrysanthemic acid for use as an intermediate in the preparation of insecticides such as deltamethrin and other pyrethrin insecticides, and because only certain optical isomers are active, alternative methods are needed to effect the separation of chrysanthemic acid's geometric isomers as well as simultaneously achieving high resolution of its enantiomers.

SUMMARY OF PRESENT INVENTION

In accordance with the present invention, effective separation of mixed geometric isomers of chrysanthemic acid to the trans form while obtaining effective optical isomer resolution can be achieved by hydrolyzing an isomeric mixture of the esters with a liver enzyme from animal sources enumerated hereinafter.

DETAILED DESCRIPTION OF THE INVENTION

The chrysanthemic acid esters which can be separated in accordance with the invention include the $C_1$ through $C_8$ alkyl esters as well as arylalkyl, haloalkyl and hydroxyalkyl esters. As used herein alkyl is intended to cover straight and branched chain alkyl groups as well as alkyl groups substituted with substituents such as halo, (chlorine, bromine or iodine,) and hydroxy. Aryl is intended to include up to two fused rings nd the halo and hydroxy substituted derivatives thereof. Preferably, the esters are the $C_1$ through $C_4$ alkyl esters. Alkyl can be illustrated by methyl, ethyl, propyl, n-butyl; haloalkyl by 2-chloroethyl; and hydroxyalkyl by 2-hydroxyethyl. Arylalkyl can be illustrated by benzyl.

The compositions which can be separated are mixed geometric isomer mixtures containing cis and trans forms. It has been found that the enzymes of the invention will separate pure trans acid from the mixed esters by hydrolysis. The method of the invention is therefore effective for separating trans acid from a mixture of cis/trans esters of chrysanthemic acid.

Chrysanthemic acid is optically active having two chiral centers. Effective use of the acid as an intermediate has dictated the resolution of the compound. The enzymes of the invention have the ability to resolve the acid into its dextro (1R, 3R) and levo-rotatory (1S, 3S) forms. The degree of resolution varies from enzyme to enzyme depending on the animal source. The effectiveness of an enzyme in resolution can be seen by the EE (enantiomeric excess).

The enzyme can be used in crude form, solvent treated or purified. Solvents which can be used to treat the enzyme include alcohols such as ethanol, hydrocarbons such as, hexane, isooctane and ketones such as acetone, preferably acetone. The use of liver acetone powders has been found to be effective in practicing the invention.

The liver enzymes found effective in separating the geometric isomers of chrysanthemic acid in accordance with the invention can be obtained from the livers of sheep, goat, bovine, dog, chicken, mouse, calf, horse, pigeon, rabbit, cat, whale and rat. Enzymes found to be ineffective include those obtained from the livers of eel, turtle, guinea pig, lemon shark, lungfish, salmon, and trout. Any liver enzyme which is effective in separating and/or resolving chrysanthemic acid to a level of 12% separation and, preferably, at least 15% EE are useful in the present invention.

The criteria for the above grouping is based on a geometric separation hydrolysis reaction which provides results greater than the use of porcine liver enzyme after 48 hours of reaction time listed in descending order of effectiveness. Preferably, and based on separation results above 15% by weight based on the weight of the initial mixture of cis and trans chrysanthemic acid after 24 hours, the enzymes can be derived from sheep, goat, bovine, dog, horse, chicken, cat, mouse and mixtures thereof. Based on a hydrolysis rate of above 25%, the most preferred enzymes are derived from sheep, goat, bovine, dog, horse, and mixtures thereof. Horse has been included in this listing because of its good EE.

From the standpoint of stereospecific resolution, and based on EE above porcine after 48 hours of reaction time, the enzymes which have been found to be effective include, horse, rabbit, pigeon, cat, seal, mouse, chicken, calf and mixtures thereof. At an EE of above 30%, after 48 hours, the more preferred enzymes are derived from the livers of horse, rabbit, pigeon, cat, seal, mouse and mixtures thereof. Above 60% EE at 48 hours of reaction time, the most preferred enzymes are derived from the livers of horse, rabbit, pigeon, cat and mixtures thereof.

Based on percent separation by hydrolysis and percent EE the best overall enzyme is derived from the liver of horse.

These listings and numbers are based on the use of liver acetone powder. The use of crude or purified enzymes may change the order. This can be easily determined by an ordinary artisan using conventional tests. It is known that crude enzymes are less effective than purified enzymes as a general concept. This is applicable to the listing of enzymes in the present invention.

Preferably, purified enzymes are utilized. The enzymes can be used free or immobilized by conventional means. The enzymes, once purified, can also be duplicated by cloning using standard techniques.

Suitable methods for immobilizing the enzymes for use herein are known in the art. See, for example, U.S. Pat. No. 4,436,813 which describes the immobilization of enzymes or cells containing the same using prepolymer materials such as polyaziridine prepolymers (i.e. Polycup), carboxymethyl cellulose, polymethylene isocyanate and polyurethane hydrogel prepolymers. Any of these materials may be used for the present purposes in the manner described in U.S. Pat. No. 4,436,813. Also useful herein for immobilizing the enzyme are curable polyfunctional aziridine prepolymers as described in U.S. Pat. No. 4,650,755 and Ser. No. 938,248, the contents of the patents and application mentioned in this paragraph being incorporated herein by reference.

The enzymatic resolution can be carried out at any temperature range which is conducive to reaction and which does not inactivate the enzymes. High temperatures (i.e. >50° C.) are conducive to enzyme inactivation. Temperatures as low as 10° C. can be used though reaction rates are considerably lower. Effective temperatures vary somewhat depending on reactants and enzymes utilized. Advantageous results have been seen at temperatures ranging from about 25° C. to about 50° C., preferably from about 30° C. to about 40° C.

The pH utilized during the resolution reaction is that pH range conducive to efficient enzymatic reaction. While each enzyme has its own particular effective pH range, it has been found that pH's in general within the range of from about 5 to about 8.5 and preferably from about 6.5 to 7.5 are effective for the enzymes disclosed herein.

The reaction time used in the resolution is that time necessary to achieve the desired extent of reaction. Reaction times vary depending on the quantity, type and purity of the enzyme and the substrate and reaction times ranging from about one-half hour to several days are illustrative.

The incubation reaction can be conducted in aqueous solution or in mixed aqueous solution/organic solvent systems. The effectiveness of the mixed aqueous solution/organic solvent systems depend on the reactant, enzyme and organic solvent. The organic solvents can be derived from such sources as hydrocarbons, aromatic hydrocarbons, ethers, alcohols, and other polar and nonpolar organic solvents. The solvents which can be used include from zero to 99% by volume water-miscible organic solvent. Water-immiscible solvents can be used with water to form a two phase solvent system, which can comprise from about zero to about 50% by volume aqueous component and corresponding from about 100% to about 50% water-immiscible organic solvent.

The water-miscible organic solvents can be illustrated by alcohols such as $C_1-C_3$ alcohols and 1 methoxy-2-propanol, glycols such as propylene glycol, glycol ethers such as dimethyl ether of ethylene glycol, dimethyl ether of propylene glycol, dimethyl ether of diethylene glycol, dimethyl ether of tetraethylene glycol, and triols such as glycerol; cyclic oxides such as tetrahydrofuran and dioxane; ketones such as acetone and nitrogen containing compounds such as acetonitrile and dimethyl formamide and mixtures thereof.

The water-immiscible organic solvents can be illustrated by hydrocarbons such as hexane, heptane, isooctane, decane, hexadecane, kerosene, petroleum ether, toluene and xylenes; chlorinated hydrocarbon such as methylene chloride and chloroform; esters such as ethyl acetate, ethers such as propyl ether, isopropyl ether, butyl ether, isobutyl ether, diethyl ether, methyl ethyl ether and diphenyl ether; and alcohols such as 2-ethyl-1-hexanol, 1-octanol, 2-octanol and mixtures thereof.

The resolved acids can be separated from the aqueous reaction solution by usual means including salting out, precipitation, extraction. The unresolved ester can be separated, racemized and recycled for further resolution.

The ethyl ester of trans chrysanthemic acid used in the following examples was purchased form Sigma Chemical Company and was a mixture of cis and trans isomers in the ratio of 35:65 and was used as such. The liver acetone powders were purchased from Sigma Chemical Company.

EXAMPLE 1

In separate scintillation vials (20 ml), 50 mg of liver acetone powder (except eel, *Anguilla anguilla*, used at 25 mg) was added along with 5 ml of 0.1M potassium phosphate buffer (pH 7) followed by 50 ul (42 mg) of the ethyl ester of chrysanthemic acid. The vials were placed in an orbital shaker and were shaken at 150 rpm at 25° C. Duplicate experiments were set up for each liver acetone powder. After 24 and 48 hours, the reactions were terminated by acidification to pH 2 by dropwise addition of 6N HCl and extracted with dichloromethane (5 ml). The dichloromethane extract was analyzed to determine (i) the type and amounts of acid produced (see Example 2) and (ii) the enantiomeric compositions of the acid produced (see Example 3).

EXAMPLE 2

A portion (0.1 ml) of the dichloromethane extract (obtained in Example was diluted with 4.9 ml methanol and analyzed by HPLC on a Partisil 5 ODS-3 RAC column (9.4 mm × 100 mm, Whatman) using mixtures of methanol and 10 mM ammonium dihydrogen phosphate in the ratio of (i) 80:20 at 2 ml/min and (ii) 50:50 at 4 ml/min and in both cases monitored by UV at 220 nm. The acid produced in all cases was the trans acid, the cis ester remained unchanged. The results are reported in Table I.

EXAMPLE 3

The acid produced was converted into its diastereomeric amides with R (+)-1-phenylethylamine as follows. A portion of the dichloromethane extract (obtained in Example 1) was dried over anhydrous sodium sulfate, filtered and cooled to 0° C. To the cooled solution in stoppered vials was added N-methylmorpholine (100 ul) followed by isobutyl chloroformate (100 ul). The mixture was gently shaken at 0° C. for 10 minutes. R(+)-1-Phenylethyl amine (100 ul) was added and the gentle shaking was continued at 0° C. for 5 minutes and at room temperature for an additional 5 minutes. The reaction mixture was successively washed with water, 1N HCl, and water. The reaction product containing the diastereomeric amides was analyzed by HPLC on a Pirkle IB covalent D-phenylglycine column (4.6 mm×25 cm, Regis Chemical Co.) using a mixture of hexane and isopropanol (95:5) at 2 ml/min monitored by UV at 220 nm. Authentic acids were also converted to the amides in the same way and analyzed by the same procedure. The acids produced in the hydrolysis were compared with the authentic specimens. The results are set forth in Table I. Enantiomeric excess (EE) is defined as the % d or l whichever is higher minus the %l or d whichever is lower. The enantiomer which predominates is reported in Table I in parenthesis under EE.

TABLE I

Hydrolysis of Ethyl Chrysanthemate by Liver Acetone Powders

| Liver acetone Powders from | After 24 hours | | After 48 hours | |
|---|---|---|---|---|
| | EE of trans acid (d or l) | Trans acid (%)* | EE of trans acid (d or l) | Trans Acid (%)* |
| Horse | 86.8 (l) | 19.1 | 86.4 (l) | 19.8 |
| Rabbit | 69.2 (l) | 13.1 | 69.6 (l) | 18.6 |
| Pigeon | 65.4 (l) | 12.6 | 63.4 (l) | 18.9 |
| Cat | 60.0 (l) | 15.7 | 63.0 (l) | 17.5 |
| Seal | 47.8 (l) | 5.6 | 47.8 (l) | 7.4 |
| Mouse | 44.8 (d) | 14.6 | 39.8 (d) | 23.9 |
| Chicken | 28.4 (l) | 16.8 | 28.8 (l) | 24.4 |
| Calf | 25.8 (l) | 12.2 | 28.8 (l) | 21.7 |
| Porcine | 30.2 (l) | 13.5 | 26.2 (l) | 11.2 |
| Bovine | 21.8 (l) | 22.5 | 22.8 (l) | 30.4 |
| Dog | 13.2 (d) | 20.0 | 19.4 (d) | 30.1 |
| Sheep | 10.0 (d) | 32.3 | 6.2 (l) | 45.0 |
| Rat | 9.0 (d) | 7.5 | 8.8 (d) | 15.1 |
| Goat | 8.8 (d) | 31.5 | 7.8 (d) | 44.6 |
| Whale | 5.0 (d) | 11.2 | 1.2 (d) | 15.8 |
| Eel(a) | — | 0 | — | 2.1 |
| Eel(b) | — | 0 | — | 1.3 |
| Lemon Shark | — | 1.6 | — | 0 |
| Lungfish | — | 1.5 | — | 1.5 |
| Salmon | — | 1.1 | — | 0 |
| Trout | — | 1.4 | — | 0 |
| Turtle | — | 0 | — | 0 |
| Guinea Pig | — | 1.0 | — | 1.4 |
| Control** | — | 0 | — | 1.4 |

Legend
*Percent of trans acid = 100 × (Trans acid)/(Trans acid + Cis ester + Trans ester). There was no trace of cis acid formed in any case.
**Control reaction contained only the ester and buffer.
— Not determined.
(a)*Anguilla anguilla*
(b)*Electrophorus electricus*

EXAMPLE 4

The hydrolysis of the ethyl ester of chrysanthemic acid was repeated using horse liver acetone powder in the same manner as described in Example 1. The products were analyzed in the same manner as described in Example 2 and the enantiomeric excess was determined as in Example 3. The results are set forth in Table II. A portion of the dichloromethane extract of the hydrolysis product was extracted with 5% sodium bicarbonate to separate the acid produced in the hydrolysis. The analysis of the washed dichloromethane solution (as in Example 2) showed the presence of only the cis and trans ethyl ester of chrysanthemic acid. This recovered ester showed a positive rotation at the sodium-D line. The sodium bicarbonate extract was acidified and extracted with dichloromethane. This second dichloromethane extract was found to contain (by analysis as in Example 2) only the trans acid and its rotation (at the sodium-D line) was also negative as expected for the l-trans acid.

TABLE II

Hydrolysis of Ethyl Chrysanthemate by Horse Liver Acetone Powder

| Time hours | Percentage in the mixture | | | | Percent of trans ester hydrolyzed | EE of l-trans acid |
|---|---|---|---|---|---|---|
| | Ester | | Acid | | | |
| | trans | cis | trans | cis | | |
| 0** | 65 | 35 | 0 | 0 | 0 | 0 |
| 24 | 49 | 38 | 13 | 0 | 21 | 86 |
| 92 | 34 | 37 | 29 | 0 | 46 | 86 |

**Composition of starting materials

What is claimed is:

1. A process for hydrolyzing the trans stereoisomer esters of chrysanthemic acid comprising
   contacting a mixture of the esters of chrysanthemic acid with an animal liver enzyme, wherein the liver enzyme is derived from an animal selected from the group consisting of horse, rabbit, pigeon and cat; and
   recovering at least one stereoisomer.

2. The process of claim 1 wherein the hydrolysis provides only one disastereoisomer of chrysanthemic acid.

3. The process of claim 1 wherein the hydrolysis provides only the trans isomer of chrysanthemic acid.

4. The process of claim 1 wherein the unreacted trans ester contains predominantly (1R, 3R)-trans chrysanthemic acid ester.

5. The process of claim 1 wherein the liver enzyme is selected from the group consisting of crude enzyme, solvent treated liver enzyme and purified liver enzyme.

6. The process of claim 5 wherein the liver enzyme is a solvent treated liver enzyme and the solvent is acetone.

7. The process of claim 1 wherein the liver enzyme is immobilized.

8. The process of claim 7 wherein the liver enzyme is immobilized by absorbing the enzyme on an ion exchange resin followed by contacting the so absorbed enzyme with a polyaziridine prepolymer.

9. The process of claim 1 comprising the preliminary step of treating the enzyme with at least one solvent selected from the group consisting of alcohols, hydrocarbons, ketones and mixtures thereof.

10. The process of claim 9 wherein the solvent is selected from the group consisting of ethanol, hexane, isooctane and acetone.

11. The process of claim 1 wherein the mixture of esters is contacted with acetone powder containing the animal liver enzyme.

12. The process of claim 11 wherein an ethyl ester of chrysanthemic acid is contacted with the enzyme.

13. The process of claim 1 wherein a mixture of trans and cis esters of chrysanthemic acid is contacted with the animal liver enzyme.

14. The process of claim 1 wherein the esters of chrysanthemic acid hydrolyzed are selected from the group consisting of $C_1$ through $C_8$ alkyl esters, arylalkyl esters, haloalkyl esters, hydroxyalkyl esters and mixtures thereof.

15. The process of claim 14 wherein the esters of chrysanthemic acid are selected from the group consisting of methyl ester, ethyl ester, propyl ester, n-butyl ester, 2-chloroethyl ester, 2-hydroxyethyl ester, benzyl ester and mixtures thereof.

16. The process of claim 15 wherein the ester is ethyl chrysanthemate.

17. The process of claim 1 wherein said hydrolyzing is carried out at a temperature of below about 50° C.

18. The process of claim 1 wherein said hydrolyzing is carried out at a temperature of about 10° C.

19. The process of claim 1 wherein said hydrolyzing is carried out at a temperature of about 25° C. to 50° C.

20. The process of claim 1 wherein said hydrolyzing is carried out at a temperature of about 30° C. to about 40° C.

21. The process of claim 1 wherein said hydrolyzing is carried out at a pH of from about 5 to about 8.5.

22. The process of claim 21 wherein said pH is from about 6.5 to about 7.5.

23. The process of claim 1 wherein said hydrolyzing ranges from about one half hour to about several days.

24. The process of claim 1 wherein said hydrolyzing is carried out in an aqueous solution or in a mixed aqueous solution-organic solvent system.

25. The process of claim 24 additionally comprising recovering one stereoisomer from solution by salting out, precipitation or extraction.

26. The process of claim 24 wherein said mixed aqueous solution-organic solvent system comprises from about zero to about 99% by volume water-miscible organic solvent.

27. The process of claim 26 wherein said water-miscible solvent is selected from the group consisting of alcohols, glycols, glycol ethers, triols, cyclic oxides, ketones, nitrogen-containing compounds and mixtures thereof.

28. The process of claim 27 wherein said water-miscible solvent is selected from the group consisting of $C_1$–$C_3$ alcohols, 1-methoxy-2-propanol, propylene glycol, dimethyl ether of tetraethylene glycol, glycerol, tetrahydrofuran, dioxane, acetone, acetonitrile, dimethyl formamide and mixtures thereof.

29. The process of claim 24 wherein said mixed aqueous solution—organic solvent system comprises from about zero to about 50% by volume aqueous component and from about 100% to about 50% water immiscible organic solvent component to form a two phase system.

30. The process of claim 29 wherein said water-immiscible solvent is selected from the group consisting of hydrocarbons, chlorinated hydrocarbons, esters, ethers, alcohols and mixtures thereof.

31. The process of claim 30 wherein said water-immiscible solvent is selected from the group consisting of hexane, heptane, isooctane, decane, hexadecane, kerosene, petroleum ether, toluene, xylenes, methylene chloride, chloroform, ethyl acetate, propyl ether, isopropyl ether, butyl ether, isobutyl ether, diethyl ether, methyl ethyl ether, diphenyl ether, 2-ethyl-1-hexanol, 1-octanol, 2-octanol and mixtures thereof.

32. A process for hydrolyzing the trans stereoisomer esters of chrysanthemic acid comprising
contacting a mixture of the esters of chrysanthemic acid with an animal liver enzyme, wherein the liver enzyme is derived from an animal selected from the group consisting of horse, rabbit, pigeon and cat; and
recovering at least one stereoisomer,
wherein the hydrolysis provides predominantly (1S, 3S)-trans chrysanthemic acid.

33. The process of claim 32 wherein an ethyl ester of chrysanthemic acid is contacted with the enzyme.

34. The process of claim 32 wherein the mixture of the esters is contacted with acetone powder containing the animal liver enzyme.

35. The process of claim 32 wherein a mixture of cis and trans esters of chrysanthemic acid is contacted with the animal liver enzyme.

36. A process for hydrolysing the trans stereoisomer esters of chrysanthemic acid comprising
contacting a mixture of the esters of chrysanthemic acid with an animal liver enzyme having a stereospecificity for the trans-chrysanthemic acid enantiomer product as measured by the enantiomeric excess after 24 hours of at least about 50,
wherein the liver enzyme is derived from an animal selected from the group consisting of horse, rabbit, pigeon and cat; and
recovering at least one stereoisomer.

37. The process of claim 36 wherein the enantiomeric excess after 24 hours is at least about 60.

38. The process of claim 37 wherein the enantiomeric excess after 24 hours is at least about 80.

39. The process of claim 36 wherein the mixture of the esters is contacted with acetone powder containing the animal liver enzyme.

40. The process of claim 36 wherein a mixture of trans and cis esters of chrysanthemic acid is contacted with the animal liver enzyme.

41. A process for hydrolyzing the ethyl ester of trans chrysanthemic acid to provide the (1S, 3S) form of trans chrysanthemic acid, comprising
contacting a mixture of trans and cis ethyl esters of chrysanthemic acid with an aceton powder containing an animal liver enzyme wherein the liver enzyme is derived from an animal selected from the group consisting of horse, rabbit, pigeon and cat; and
recovering predominantly the (1R, 3R) form of the ethyl ester of trans chrysanthemic acid and the (1S, 3S) form of trans chrysanthemic acid,
wherein the hydrolysis predominantly provides the (1S, 3S) form of trans chrysanthemic acid.

* * * * *